(12) United States Patent
Nguyen et al.

(10) Patent No.: US 9,226,797 B2
(45) Date of Patent: Jan. 5, 2016

(54) COMPUTER AIDED IMPLANTATION OF BODY IMPLANTS

(71) Applicants: Phi Nguyen, Houston, TX (US); Loc Phan, San Jose, CA (US); Bao Tran, Saratoga, CA (US); Thuan Nguyen, Houston, CA (US); Duy Bui, Ha Noi (VN)

(72) Inventors: Phi Nguyen, Houston, TX (US); Loc Phan, San Jose, CA (US); Bao Tran, Saratoga, CA (US); Thuan Nguyen, Houston, CA (US); Duy Bui, Ha Noi (VN)

(73) Assignee: MIBA Medical Inc., San Jose, CA (US)

( * ) Notice: Subject to any disclaimer, the term of this patent is extended or adjusted under 35 U.S.C. 154(b) by 0 days.

(21) Appl. No.: 14/255,952

(22) PCT Filed: Dec. 17, 2012

(86) PCT No.: PCT/VN2012/000008
§ 371 (c)(1),
(2) Date: Apr. 17, 2014

(87) PCT Pub. No.: WO2014/100837
PCT Pub. Date: Jun. 26, 2014

(65) Prior Publication Data
US 2015/0289945 A1    Oct. 15, 2015

Related U.S. Application Data

(60) Provisional application No. 61/722,221, filed on Nov. 4, 2012.

(51) Int. Cl.
| | | |
|---|---|---|
| A61F 2/12 | (2006.01) | |
| A61B 19/00 | (2006.01) | |
| A61F 2/02 | (2006.01) | |
| A61L 27/36 | (2006.01) | |
| A61M 5/20 | (2006.01) | |
| A61L 27/36 | (2006.01) | |
| A61M 5/20 | (2006.01) | |

(52) U.S. Cl.
CPC . *A61B 19/50* (2013.01); *A61F 2/02* (2013.01); *A61F 2/12* (2013.01); *A61L 27/3633* (2013.01); *A61M 5/20* (2013.01); *A61B 2019/504* (2013.01); *A61B 2019/505* (2013.01); *A61F 2250/0003* (2013.01)

(58) Field of Classification Search
CPC ................................. A61F 2/12; G06F 17/50
USPC .......................................................... 623/7–8
See application file for complete search history.

(56) References Cited

U.S. PATENT DOCUMENTS

| | | | |
|---|---|---|---|
| 6,546,279 B1 | 4/2003 | Bova | |
| 7,587,075 B1 | 9/2009 | Stefan | |
| 8,167,836 B2 * | 5/2012 | Lee | A61B 19/24 604/103 |
| 8,864,843 B2 * | 10/2014 | Lu | A61K 38/18 623/23.72 |
| 2008/0232545 A1 * | 9/2008 | Wu | A61B 6/025 378/22 |
| 2009/0024215 A1 * | 1/2009 | Lesh | A61M 29/02 623/11.11 |
| 2009/0181104 A1 | 7/2009 | Rigotti et al. | |
| 2010/0292963 A1 * | 11/2010 | Schroeder | A61F 2/30 703/1 |
| 2011/0053132 A1 * | 3/2011 | Glicksman | G09B 23/34 434/267 |
| 2011/0137244 A1 * | 6/2011 | Lee | A61B 19/24 604/103.02 |
| 2011/0142936 A1 * | 6/2011 | Campbell | A61L 27/50 424/484 |
| 2011/0168185 A1 * | 7/2011 | Schottdorf | A61B 6/04 128/845 |
| 2013/0245801 A1 * | 9/2013 | Schroeder | A61F 2/30 700/98 |
| 2014/0017651 A1 * | 1/2014 | Sugimoto | G09B 23/30 434/272 |

FOREIGN PATENT DOCUMENTS

WO        WO02040072 A3    9/2002

* cited by examiner

*Primary Examiner* — Suzette J Gherbi
(74) *Attorney, Agent, or Firm* — Tran & Associates

(57) ABSTRACT

Systems and methods are disclosed for cosmetic injection. The apparatus includes a processor; a 3D imaging system coupled to the processor; and an injector controlled by the processor to inject filler into a patient.

20 Claims, 4 Drawing Sheets

| |
|---|
| Capture 3D model of patient (50) |
| Isolate breast or butt region (52) |
| Model shape and size of breast or butt increase due to implant (54) |
| Morph or project the shape/size of breast or butt increase onto the 3D model of patient (56) |
| Allow user to iterative change balloon shapes/sizes until satisfied with new shape (58) |
| Allow user to select from a library of wardrobes to provide realistic simulation (60) |
| Monitor injection into patient and provide feedback to professionals on additional injections if needed to achieve desired shape and size (62) |

FIG. 2A

| |
|---|
| Capture a 3D model of a patient body portion using one or more cameras (70) |
| Model shaping and size change in the body portion due to an implant (72) |
| Iteratively changing body shapes or sizes until the patient is satisfied with a desired shape or size (74) |
| Control an automatic injector to deliver the implant in the patient (76) |
| Monitor injection into patient and providing feedback if needed to achieve the desired shape and size (78) |

FIG. 2B

COMPUTER AIDED IMPLANTATION OF BODY IMPLANTS

This application claims priority to Provisional Application Ser. 61/722,221 filed Nov. 4, 2012 and a national conversion of PCT Application Serial PCT/VN2013/000001 filed Apr. 12, 2013, PCT/VN2013/000002 filed Apr. 12, 2013, PCT/VN2013/000003 filed on Apr. 12, 2013, PCT/VN2013/000004 filed Apr. 12, 2013, and PCT/VN2012/000008 filed Dec. 17, 2012, the content of which is incorporated by reference.

BACKGROUND OF INVENTION

This present invention relates to soft tissue augmentation of the human body, mainly the face, breast and buttocks.

Augmenting or changing the shape of the soft tissue of the human body has been done previously in medicine by harvesting donor tissue from one part of the body then processing and introducing it to another desired part of the body or by using implants. The donor tissue is usually adipose or fatty tissue or muscle and the harvesting of the donor tissue is time consuming and often leaves an unwanted defect and scars from the harvested site. The procedure time is lengthened with the harvesting and processing of the tissue and adds greatly to the cost of the procedure and the recovery time is also prolonged. The donor tissue will then have to be placed in the desired area usually through surgical means which can be lengthy and costly and usually laves a large scar as in the case of the breast or buttocks (butts).

Reconstruction of the human breast or butt involves introducing a fixed or changeable-volume sac-like silicone rubber structure into a body cavity surgically created to receive such an implant. The implants and coverings therefore are described, by way of illustration and not by limitation, in: Braumann U.S. Pat. No. 4,648,880; Hamas U.S. Pat. No. 4,531,244; Ledergerber U.S. Pat. No. 4,955,907, Corbitt U.S. Pat. No. 6,881,226, Kinsley U.S. Pat. No. 6,981,988, and Studin U.S. Pat. No. 7,137,995, the contents of which are incorporated by reference.

Known methods of augmentation mammoplasty utilize silicone or saline implants. These methods have been complicated post-operatively by encapsulation of the implants, which can occur to varying degrees. Encapsulation produces a hard area of scar tissue around the implant, resulting in a rigid, abnormally-shaped mound beneath the breast or butt tissue or pectoralis muscle, depending upon the placement of the implant.

The usual skin incision is on the order of 3-8 centimeters in length and is stretched open with retractors to facilitate the introduction of the implant. In various surgical procedures, a breast or butt implant is placed within the surgically formed body cavity for subsequent inflation and/or deflation with a fluid.

In plastic and reconstructive surgery, when a breast or butt implant or tissue expander is placed in the dissected pocket, it is typically filled via a fill connector coupled to fill tubing which is attached to a filling material (e.g. saline solution) source.

There are currently three basic types of fill connectors used to connect the fluid source to the implant, the choice of which often depends on the implant and the particular surgical approach used. The first is a permanent attachment of the fill tubing to the implant. A common means for this attachment is to make a small opening within the body or shell of the implant and insert the tubing securing it by means of connecting materials such as sleeves, patch assemblies, adhesives or vulcanizing compounds.

The other two common connectors are for temporary attachment of the fill tubing to the implant by means of a valve in the implant which seals after the fill tubing is removed. One of these two temporary attachment means is most commonly used with saline-fill breast or butt implant devices that include a diaphragm valve within the shell. The valve has an opening that requires a rigid male implement to be inserted in the opening thus opening the valve and allowing fluid transfer. This male implement is the fill tip end of the fill connector, which has on the opposite end one or more barbs which accept the flexible (e.g. silicone or vinyl) fill tubing. In use, the fill connector and fill tubing attach to the implant normal to the implant surface.

Since breast or butt implants are usually placed into the body through incisions considerably smaller than the implant, it has always been a challenge to introduce them. With greatly increased friction at the interface between the surface of newer texturized implants and the wound margins (body tissue), it has become correspondingly more difficult to introduce these implants. Increased manipulation of both implants and patient tissue often results in trauma to both implants and patient tissue, thereby increasing the risk associated with the procedure both in terms of immediate consequences as well as delayed structural failure and the implications deriving therefrom. Postoperative infection has also been a troublesome consequence of the need to manipulate the implant into place.

In a related art, U.S. Pat. No. 7,491,709 discloses methods of providing long-term minimization of wrinkles or folds in the skin by injecting a bolus of hyaluronic acid deep into the skin. The methods of the present invention are particularly beneficial for improving the contours of the cheeks, filling folds under the eyes, and providing the visual effect of a chin implant, without requiring the use of surgical procedures.

United States Patent Application 20090240200 discloses a system for inserting a distal end portion of a needle of a medical injector into a skin of a body. An energy source operatively coupled to the medical injector is actuated such that a dermal filler is conveyed from the medical injector into the skin through the distal end portion of the needle. The distal end portion of the needle is moved within the skin during the actuating.

SUMMARY OF THE INVENTION

In one aspect, computerized planning tools are provided to enable doctors to plan specific injection sites to achieve desired cosmetic effects on the patients. The tools can guide the doctors or professionals to achieve the desired effects.

In another aspect, an apparatus for cosmetic injection includes a processor; a 3D imaging system coupled to the processor; and an injector controlled by the processor to inject filler into a patient.

In another aspect, a method to perform cosmetic enhancements includes capturing a 3D model of a patient body portion using one or more cameras; modeling shape and size change in the body portion due to an implant; iteratively change body shapes or sizes until the patient is satisfied with a desired shape or size; controlling an automatic injector to deliver the implant in the patient; and monitoring injection into patient and providing feedback if needed to achieve the desired shape and size.

Implementations of the above aspects may include on or more of the following. The system includes morphing or project the shape/size of breast or butt increase onto the 3D model of patient. A user can select from a library of wardrobes to provide realistic post-implant simulation. The system can inject a polymer into the shell of a soft tissue human implant prior to or during implantation of the shell with a lumen in a human body. The system can cross-link the polymer, wherein a cross linking reaction occurs outside the shell or in-situ inside the shell. The polymer can be one of: collagens, hyaluronic acids, celluloses, proteins, saccharides. The polymer can be an extracellular matrix of a biological system. Cross linkers can be used to from homo-polymers or to form copolymers by crosslinking with other polymer species. The filler material can control drug releases at predetermined timing in anticipation of an onset of a negative physiological event in response to invading foreign bodies. The system can inject anesthetics, lidocaine or compound to reduce or eliminate acute inflammatory reactions to the pharmaceutical substance. One or more compositions can be added and be selected from the group consisting of steroids, corticosteroids, dexamethasone, triamcinolone. The injector includes a medicament container, a needle, an energy source, and a regulator. The injector medicament container has a piston movably disposed therein such that the medicament container is divided into a first portion and a second portion. The first portion of the medicament container is configured to contain a filler, wherein the needle is coupled to the medicament container such that the needle is in fluid communication with the first portion of the medicament container. The methods include injecting a bolus of hyaluronic acid deep into the skin.

Other implementations of the above aspect can include one or more of the following. The system can be implanted through a cannula or needle, and can be filled with medicaments or chemical agents that would be useful in treating the patient including beneficial medications, chemical agents, hormonal treatments, stem cells, such as adipocytes, cellular precursors and components, and radiation media can be instilled to enhance the treatment capabilities of the implant in cancer and other breast or butt pathology.

Advantages of the preferred embodiments may include one or more of the following. The methods of the present invention are particularly beneficial for improving the contours of the breast or butts or buttocks, without requiring the use of surgical procedures. The system alleviates the difficulty of introducing breast or butt implants, and thus limiting greatly both the damage to implants and trauma to patient tissues. The system greatly reduces the need to manipulate the breast or butt implant in to place in the formed body cavity, and as a consequence greatly reduces postoperative infection. The hyaluronic acid enables soft tissue augmentation of the human body such as face, breast, buttocks and any soft tissue areas of the body. The injectable solution fills up the soft tissue are in question and is absorb by the body over the course of several months to a year. This injection alleviates the need for anesthesia and surgical placement of breast or butt or buttocks implants or autologus fat harvesting and injections. The entry wound is a small puncture and leaves no large permanent scars like the surgical approach. Since it is minimally invasive, the recovery time is much quicker and the down time from the procedure is almost eliminated completely. The system is ideal for the lean, athletic individual who doesn't have any fat to transfer and because of the high metabolic rate of the said individual it would burn the fat off anyway. The system would allow easy soft tissue augmentation in these types of patients. The easy non-surgical deployment of the system allows quick and easy soft tissue augmentation of the body whether it be for cosmetic such as breast or butt augmentation, buttocks augmentation, facial rejuvenation, and penile augmentation (enlargement), or reconstructive purposes where the is a soft tissue defect and lack of donor material. The soft tissue can easily be augmented precisely, quickly, with minimal recovery and scaring from a surgical incision by using the system any time that the needs arises without the need for fat harvesting, anesthesia, or surgery.

BRIEF DESCRIPTION OF THE DRAWINGS

FIGS. 2A-2B show exemplary processes that work with the system of FIG. 1

DESCRIPTION

As a preface to the detailed description, it should be noted that, as used in this specification and the appended claims, the singular forms "a", "an", and "the" include plural referents, unless the context clearly dictates otherwise. All percentages (%) listed for gas constituents are % by volume, unless otherwise indicated.

The term "hyaluronic acid" (HA) as used in the present application refers to hyaluronic acid or salts of hyaluronic acid, such as the sodium, potassium, magnesium and calcium salts, among others. The term "hyaluronic acid" is also intended to include not only elemental hyaluronic acid, but hyaluronic acid with other trace of elements or in various compositions with other elements, as long as the chemical and physical properties of hyaluronic acid remain unchanged. In addition, the term "hyaluronic acid" as used in the present application is intended to include natural formulas, synthetic formulas or combination of these natural and synthetic formulas.

Figure 1:
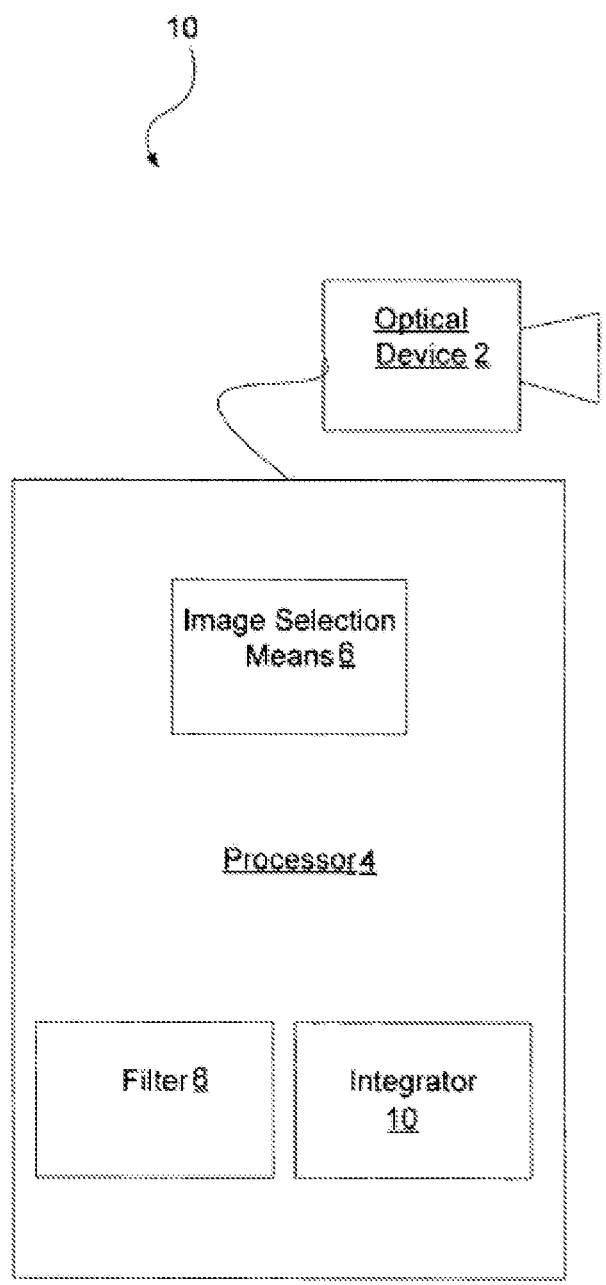
FIG. 1 shows an exemplary system to aid medical professionals such as doctors, plastic surgeons, and nurses to perform cosmetic enhancements on a patient.

FIG. 1 shows an exemplary system to aid medical professionals such as doctors, plastic surgeons, and nurses to perform cosmetic enhancements on a patient. In this system, the 3D imaging system (10) generally includes a camera or optical device (2) for capturing 3D images and a processor (4) that processes the 3D images to construct a 3D model. According to one exemplary embodiment illustrated in FIG. 1, the processor (4) includes means for selecting 3D images (6), a filter (8) that removes unreliable or undesirable areas from each selected 3D image, and an integrator (10) that integrates the 3D images to form a mosaic image that, when completed, forms a 3D model. The optical device (2) illustrated in FIG. 1 can be, according to one exemplary embodiment, a 3D camera configured to acquire full-frame 3D range images of objects in a scene, where the value of each pixel in an acquired 2D digital image accurately represents a distance from the optical device's focal point to a corresponding point on the object's surface. From this data, the (x,y,z) coordinates for all visible points on the object's surface for the 2D digital image can be calculated based on the optical device's geometric parameters including, but in no way limited to, geometric position and orientation of a camera with respect to a fixed world coordinate, camera focus length, lens radial distortion coefficients, and the like. The collective array of (x,y,z) data corresponding to pixel locations on the acquired 2D digital image will be referred to as a "3D image". Alternatively, the 3D camera can simply be two cameras spaced apart at a predetermined distance to provide 3D perspective capture. 3D image integration can be done using pre-calibrated camera positions to align multiple 3D images to merge the aligned 3D images into a complete 3D model. More specifically, cameras can be calibrated to determine the physical relative position of the camera to a world coordinate system. Using the calibration parameters, the 3D images captured by the camera are registered into the world coordinate system through homogeneous transformations. While traditionally effective, this method requires extensive information about the camera's position for each 3D image, severely limiting the flexibility in which the camera's position can be moved. The data capture can be viewed in an exemplary modeling system, according to one exemplary embodiment. The exemplary modeling system can support 3D image acquisition or capture, visualization, measuring, alignment and merging, morphing, editing, compression and texture overlay, all controlled using a database manager.

In one embodiment, the system photographs a patient's body in 3D before her breast or butt procedure, captures linear and volumetric measurements, and creates an exact three dimensional replica of her body on screen. The doctor examines this model with the patient during the consultation, and performs a virtual breast or butt augmentation, breast or butt lift, or breast or butt reconstruction on the 3D model to visualize the expected result in advance of an actual surgical procedure. The photorealistic result can be viewed from all angles, and implant size adjusted to most closely meet the patient's needs. This allows women for the first time to select implant size, shape, and position based on the expected outcome on their own body.

In another embodiment, a 3D webcam is used with two cameras spaced roughly the same distance apart as human eyes, for the stereoscopic effect. 3D data acquisition and object reconstruction can be performed using stereo image pairs. Stereo photogrammetry or photogrammetry based on a block of overlapped images is the primary approach for 3D mapping and object reconstruction using 2D images. Close-range photogrammetry where cameras or digital cameras can be used to capture the close-look images of objects, e.g., breast or butts, and reconstruct them using the very same theory as the aerial photogrammetry.

Once the 3D model of the implant is finalized, the patient may wish to view the "try on" implants in combination with various articles of clothing to more fully determine how the implants will affect the patient's appearance. A library of wardrobe can be placed over the patient, so the patient can preview her implants with various items of clothing. Photo-realistic images of the patient can be generated for the patient to consult family or friends as to which size implants gives the most favorable appearance. Thus, the system provides patients with the ability to realistically determine how a range of implant sizes will change their appearance.

A relatively large amount of hyaluronic acid, for example an entire syringe, is emptied into one area creating a large volume of the hyaluronic acid material in the deep tissue that does not break down readily. The deep volume or bolus can be sculpted by the doctor to enlarge or change the shape of the buttock or breast. The system injectable material comes in packages of 25, 50, 100, and 200 cc in volume. The delivery system is completely sterile and can be used in an outpatient setting or doctor's office. Since the volume of the system can be adjusted accordingly by the physician, the amount of soft tissue augmentation is limited only by the site. The system can also be additive just like MIBA Medical's Restor, Restylane or Allergan's Juvederm for augmenting facial wrinkles.

In yet another embodiment, an anti-inflammatory drug coating can be added to the hyaluronic acid injection. Exemplary drugs can include dexamethasone sodium acetate and other similar drugs used widely in pace makers and defibrillator leads system. An example list of drugs is as follows:

Anti-inflammatory (arthrotec, asacol, auralgan, azulfidine, bextra, celestone, daypro, deltasone, diclofenac, etodolac, indocin, ketoprofen, iodine, mobic, nabumetone, naproxen, piroxicam, ponstan, prednisone, rofecoxib, salofalk, solumedrol).

Antibiotics (Amlodipine, Besylate, Amoxicillin, Amoxil, Amphotericin, Ampicillin, Augmentin, Avelox, Bactrim, Bactroban, Biaxin, Ceftriaxone, Cefzil, Cephalexin, Chloramphenicol, Cipro XR, Clostebol, Cloxacillin, Cotrim, Daraprim, Dicloxacillin, Doxycycline, Eryacne, Erythromycin, Ethambutol)

Anti-aging compounds

Anti-oxidants

In another embodiment, a mixture of polyglycollic acid (PGA), and cross-linked hyaluronic acid (HA) can be used. These mixtures are combined in a foam/gel like injectable much similar to shaving cream/gel. This mixture also incorporates a broad spectrum antibiotic and corticosteroids to help prevent infection and reduce swelling. This way after introducing it into the subcutaneous soft tissue area to be augmented, it will fill up and be moldable and shapeable to the desired shape. The porous nature of the injectable allows the body to naturally fill up with the body natural fluids making it very natural in feel and look.

In one embodiment, one or more of these drugs may be incorporated into gel formulation to affect controlled delivery. The level of control over the delivery of the drug depends on the interaction between the specific drug and the polymer. The interactions are usually at the functional group level. The properties that affect the controls on the delivery are solubility, diffusion, and permeability between the polymer and the drug or drugs.

In yet another embodiment, a biocompatible polymer with a modulus that matches the modulus of the surrounding tissue may be used for natural feel and appearance. The polymer is a hydrogel that will absorb a preset amount of water will be used to control the specific desired modulus. To control the shape of the polymer, the outer surface maybe lightly crosslinked so that it will not flow into locations that are not desired. The cross-linking is gradient and light enough so that it will more elastomeric.

The system also provides improved methods of delivering sustained therapeutic dosages of medicines for extended periods. This would be more convenient to patients and reduce occurrences of missed doses. In one embodiment where the implant provides injectable medicines, the implant with drugs contained therein can maintain therapeutic levels for weeks or longer. Zero-order kinetics, wherein blood levels of drugs would remain constant throughout the delivery period. This delivery is useful in certain classes of medicines intended, for example, for antibiotic delivery, heart and blood pressure maintenance, pain control, and antidepressants.

The system allows a user to select an implant size using computer aided model using high definition web cameras (webcams) that are inexpensively manufactured and therefore made widely available. The system is easy to use such that persons with no special knowledge or training can use the 3D modeling of the body in the privacy of their home. And finally, the system provides patients with the ability to realistically determine how a range of implant sizes will change their appearance.

FIG. 2A shows an exemplary process executed by the hardware of FIG. 1. In this process, the system captures 3D model of patient (50). The process then isolates the patient's breast or butt region (52). Next, the process models shape and size of breast or butt increase due to implant (54) and morphs or projects the shape/size of breast or butt increase onto the 3D model of patient (56). The process allows the professional or the patient to iterative change implant shapes/sizes until the patient is satisfied with new shape (58). The process can also allow the user to select from a library of wardrobes to provide realistic simulation (60). When the patient selected his or her shape/size, then the system guides the professional to inject provides feedback to the professional to deliver body sculpting material to the patient (62).

FIG. 2B shows another embodiment to augment human body portions. The process includes capturing a 3D model of a patient body portion using one or more cameras (70); modeling shape and size change in the body portion due to an implant (72); iteratively change body shapes or sizes until the patient is satisfied with a desired shape or size (74); controlling an automatic injector to deliver the implant in the patient (76); and monitoring injection into patient and providing feedback if needed to achieve the desired shape and size (78).

Figure 3:
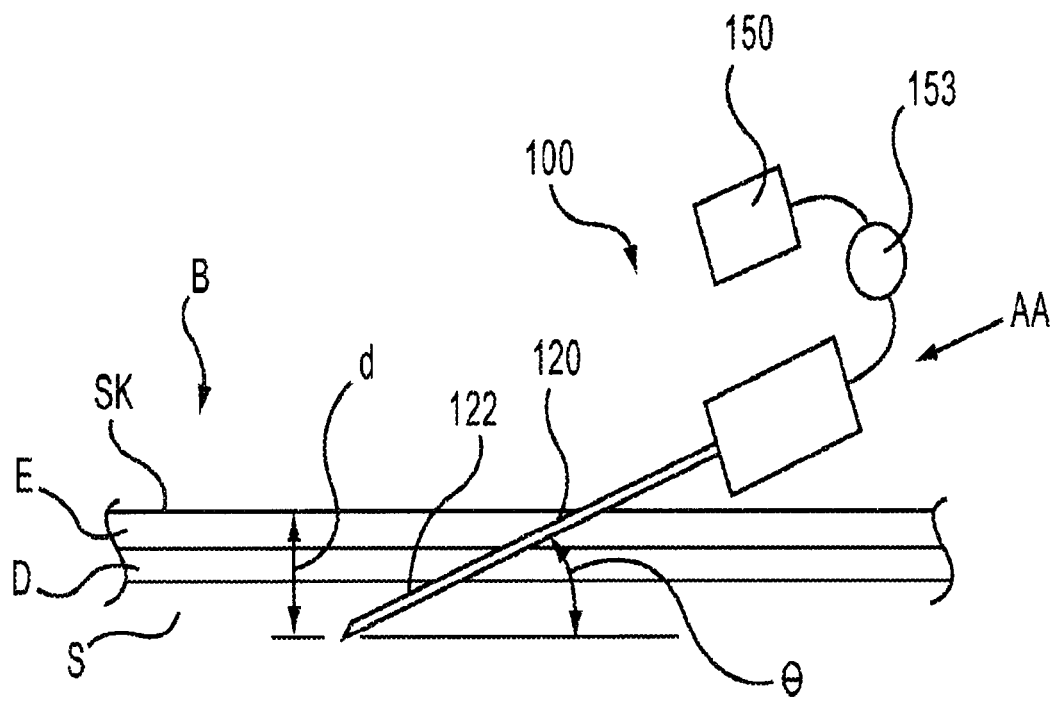
FIGS. 3-4 show exemplary halyuronic acid filler injector devices.
Figure 4:
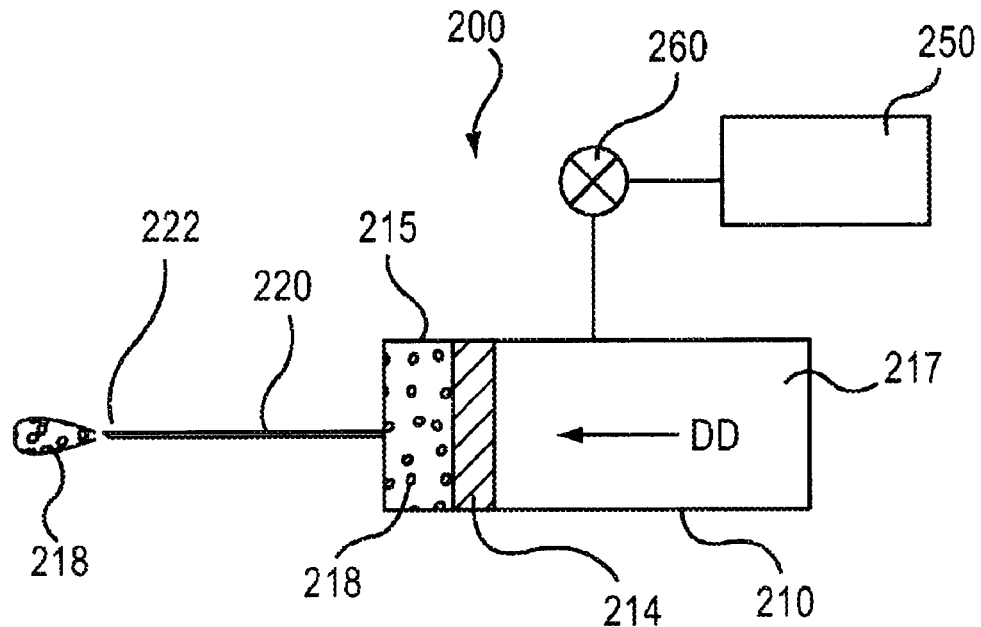

In one embodiment, the computer controls the automatic injector to fill the patient body portion to the correct shape and size. One exemplary injector is shown in FIGS. 3 and 4. FIG. 3 is a schematic illustration showing a portion of a body B containing a breast or butt filler 118 injected therein. The illustrated method includes inserting a distal end portion of a needle of a medical injector into a skin of a body. The skin can be disposed at any location of the body, such as for example, facial skin. Referring to FIG. 3, the distal end portion 122 of the needle 120 is inserted into the skin SK in a distal direction as shown by the arrow AA. The needle 120 is inserted into the skin SK at an angle Θ relative to the surface of the skin SK and at depth d within the body B. The needle 120 can be inserted into the skin SK at any suitable angle Θ and at any suitable depth d for achieving the desired result. In some embodiments, for example, the needle 120 is inserted into the skin SK at an angle Θ of between 5 and 35 degrees. In other embodiments, the needle 120 is inserted into the skin SK at an angle Θ of approximately 20 degrees. In some embodiments, for example, the needle 120 is inserted into the skin SK at a depth d of between 1.5 and 6 millimeters. In other embodiments, the needle 120 is inserted into the skin SK at a depth d of between approximately 1.5 and 2 millimeters. Although the distal end portion 122 of the needle 120 is shown as being inserted into the subcutaneous tissue S of the skin SK, in some embodiments, the distal end portion 122 of the needle 120 can be inserted into the epidermis E and/or the dermis D of the skin SK. In other embodiments, the distal end portion 122 of the needle 120 can be inserted below the subcutaneous tissue S. In yet other embodiments, the distal end portion 122 of the needle 120 can be inserted through the skin SK into another portion of the body B, such as for example a urinary sphincter. An energy source operatively coupled to the medical injector is actuated such that a breast or butt filler is conveyed from the medical injector into the skin through the distal end portion of the needle. The energy source 150 is actuated via an actuator 153. The energy source 150 can include any suitable form of energy that can act upon the medical injector 100 to convey the breast or butt filler 118 from the medical injector 100 through the distal end portion 122 of the needle 120. For example, in some embodiments, the energy source 150 can include a pressurized gas that exerts a force on a portion of the medical injector 100. When the energy source 150 is actuated by the actuator 153, the breast or butt filler 118 is conveyed from the medical injector 100 through the distal end portion 122 of the needle 120. In this manner, the breast or butt filler 118 can be injected into the body B non-manually. Said another way, the breast or butt filler 118 can be injected into the body B without the user producing the energy necessary for the injection.

The distal end portion of the needle is moved within the skin when the energy source is being actuated. In this manner, the user can vary the location of the distal end portion of the needle within the skin when the breast or butt filler is being injected into the body B. The distal end portion 122 of the needle 120 can moved in a proximal direction, when the energy source 150 is being actuated. In this manner, the user can inject a substantially continuous bead of breast or butt filler 118 along a desired passageway (e.g., a breast or butt implant) within the skin SK. More particularly, the distal end portion 122 of the needle 120 is moved in a direction substantially opposite the direction of flow of the breast or butt filler 118 from the distal end portion 122 of the needle 120.

Because the body sculpting filler 118 is conveyed from the distal end portion 122 of the needle 120 non-manually, the user is not burdened with producing a force in the distal direction (to inject the filler 118) while simultaneously moving the distal end portion 122 of the needle 120 in the proximal direction. In this manner, the operation of producing a force to inject the filler 118 is independent from the operation of moving the distal end portion 122 of the needle 120. Similarly stated, the operation of producing a force to inject the filler 118 is decoupled from (i.e., is separate and distinct from) the operation of moving the distal end portion 122 of the needle 120. This arrangement can result in a repeatable, continuous and/or controlled movement of the distal end portion 122 of the needle 120 and/or injection of the filler 118. In contrast, some known medical injectors require the user to use the same hand to produce a force in a distal direction along a longitudinal axis of the medical injector to inject a breast or butt filler and move the needle along the longitudinal axis, for example, in an opposite (i.e., proximal) direction. In such instances, the injection of the breast or butt filler can be irregular, uncontrolled and/or discontinuous. For example, when injecting high viscosity breast or butt fillers using known medical injectors, it can be difficult for the user to maintain the force necessary to inject the breast or butt filler at the desired flow rate throughout the injection event. Thus, when injecting high viscosity fillers using known medical injectors, the resulting bead of breast or butt filler can have undesirable spatial variability in its size and/or volume.

Although the distal end portion 122 of the needle 120 is shown and described above as being moved in the proximal direction when the energy source 150 is being actuated, in other embodiments, the distal end portion 122 can be moved in any manner. For example, in some embodiments the distal end portion 122 of the needle 120 can be moved in a distal direction (i.e., in substantially the same direction as the flow of the breast or butt filler 118 from the distal end portion 122 of the needle 120). In other embodiments, the distal end portion 122 of the needle 120 can be moved in a direction not parallel to a longitudinal axis of the needle 120. In yet other embodiments, the distal end portion 122 of the needle 120 can be rotated when the energy source 150 is being actuated. For example, in some embodiments, the user can "fan" the distal end portion 122 of the needle 120 (i.e., move the distal end portion 122 in a direction not parallel to a longitudinal axis of the needle 120) within the skin SK when the energy source is being actuated. Moreover, the distal end portion 122 of the needle 120 can be moved any suitable distance when the energy source 150 is being actuated. In some embodiments, for example, the distal end portion 122 of the needle 120 can be moved a distance of at least 4 millimeters during actuation of the energy source 150.

Returning to the flow chart shown in FIG. 1, in some embodiments, the method can optionally include regulating a flow rate of the breast or butt filler through the distal end portion of the needle when the energy source is being actuated, at 18. In this manner, the user can adjust the amount the breast or butt filler being injected within and/or beneath the skin to provide the desired cosmetic and/or therapeutic results. In some embodiments, for example, the flow rate of the breast or butt filler can be regulated to maintain a substantially constant flow rate of the breast or butt filler through the distal end portion of the needle when the distal end portion of the needle is moved within and/or beneath the skin. Said another way, in some embodiments, the flow rate of the breast or butt filler can be regulated to produce a substantially uniform bead of breast or butt filler within the skin. In some embodiments, for example, the flow rate of the breast or butt filler can be regulated when the needle is moved within the skin to produce a substantially uniform bead of breast or butt filler having a volume of approximately 1 to 2 cubic centimeters and a length of between approximately 4 millimeters and 13 millimeters. In other embodiments, the flow rate of the breast or butt filler can be regulated when the needle is moved within the skin to produce a substantially uniform bead of breast or butt filler having a volume of less than 1 cubic centimeter and a length of between approximately 4 millimeters and 13 millimeters. For example, in some embodiments, the flow rate of the breast or butt filler can be regulated when the needle is moved within the skin to produce a substantially uniform bead of breast or butt filler having a volume of approximately 0.1 to 0.2 cubic centimeter and a length of between approximately 4 millimeters and 13 millimeters. In yet other embodiments, the flow rate of the breast or butt filler can be regulated when the needle is moved within the skin to produce a substantially uniform bead of breast or butt filler having a volume of greater than 2 cubic centimeter (e.g., a volume of 3, 4, 5, or 10 cubic centimeters) and a length of up to 150 millimeters. Such a bead can be used, for example, to increase the skin volume in the areas of the nasal labial fold, the jowls and/or the neck region, and can smooth the appearance of wrinkles in those areas. The flow rate of the breast or butt filler can be regulated to produce any suitable flow rate. For example, in some embodiments, the flow rate of the breast or butt filler can be regulated to a substantially constant flow rate of at least approximately 0.02 cubic centimeters per minute. In other embodiments, the flow rate of the breast or butt filler can be regulated to a substantially constant flow rate of between approximately 0.02 cubic centimeters per minute and 0.5 cubic centimeters per minute. In yet other embodiments, the flow rate of the breast or butt filler can be regulated to a substantially constant flow rate of as much as 3 cubic centimeters per minute. In still other embodiments, the flow rate of the breast or butt filler can be regulated to a substantially constant flow rate greater than 3 cubic centimeters per minute. Although the flow rate of the breast or butt filler through the distal end portion of the needle is described above as being regulated to a substantially constant value when the needle is moved within the body, in some embodiments, the flow rate of the breast or butt filler can be selectively varied during the injection process. In this manner, the user can produce a bead and/or set of beads of breast or butt filler within the skin having spatially varied volume. Moreover, in some embodiments, the method 10 can include optionally regulating a flow rate of the breast or butt filler through the distal end portion of the needle such that the flow rate is substantially zero at a first time after the needle has been moved and still remains in the skin. In some embodiments, the system can include optionally stopping the flow of the breast or butt filler through the distal end portion of the needle after the needle has been moved within the skin. The distal end portion of the needle can then be moved while the flow rate of the breast or butt filler through the distal end portion of the needle is zero. The flow rate of the breast or butt filler through the distal end portion of the needle can then be regulated such that the flow rate is increased greater than zero. In this manner, the user can produce a discontinuous bead and/or set of beads of filler within the skin. In some embodiments, for example, the flow rate of the breast or butt filler through the distal end portion of the needle can be regulated such that at least one discrete bead from the set of beads has a volume of approximately 0.1 cubic centimeters or less. In other embodiments, the flow rate of the breast or butt filler through the distal end portion of the needle can be regulated such that at least one discrete bead from the set of beads has a volume of less than approximately 0.01 cubic centimeters or less. In some embodiments, the flow rate of the breast or butt filler through the distal end portion of the needle can be regulated to produce such a set of discontinuous beads in areas of the skin surrounding the eye.

The flow rate of the breast or butt filler through the distal end portion of the needle can be regulated in any suitable manner. For example, the flow rate of the breast or butt filler 118 through the distal end portion 122 of the needle 120 can be regulated by selectively controlling the energy from the energy source 150 to the medical injector 100. Said another way, in some embodiments, the flow rate of the breast or butt filler 118 through the distal end portion 122 of the needle 120 can be regulated by mechanisms outside of the flow path of the breast or butt filler 118. Moreover, in some embodiments, the flow rate of the breast or butt filler 118 through the distal end portion 122 of the needle 120 can be regulated via the actuator 153. For example, in some embodiments, the user can repeatedly and/or controllably actuate the energy source 150 using the actuator 153. Said another way, in some embodiments, the user can repeatedly toggle the actuator 153 to selectively couple the energy source 150 to and decouple the energy source 150 from the medicament injector 100. In this manner, for example, the flow rate of the breast or butt filler can be regulated to produce a discontinuous bead and/or set of beads of breast or butt filler within the skin, as described above. In other embodiments, the flow rate of the breast or butt filler 118 through the distal end portion 122 of the needle 120 can be regulated by selectively restricting the flow path of the breast or butt filler 118 within the medical injector 100 and/or the needle 120. For example, in some embodiments, the flow rate of the breast or butt filler 118 through the distal end portion 122 of the needle 120 can be regulated by a valve within the medicament flow path.

FIG. 4 illustrates a medical device 200, according to an embodiment configured inject a medicament 218. The medical device 200 includes a medicament container 210, a needle 220, an energy source 250 and a regulator 260. The medicament container 210 includes a piston 214 movably disposed therein, such that the medicament container 210 is divided into a first portion 215 and a second portion 217. In some embodiments, for example, the piston 214 can be disposed within the medicament container 210 such that the first portion 215 of the medicament container 210 is fluidically isolated from the second portion 217 of the medicament container 217.

The first portion 215 of the medicament container 210 is configured to contain a medicament 218 having a high viscosity (i.e., a medicament having a viscosity of at least 100 Poise). The medicament 218 can be any medicament suitable for being injected into a body. For example, in some embodiments, the medicament 218 can be a high viscosity dermal filler (e.g., a liquid dermal filler, a paste-like dermal filler, a dermal filler including both a liquid component and a solid component, or the like). In some embodiments, the medicament 218 can have a viscosity of at least 1000 Poise (100 N-sec/m2). In other embodiments, the medicament 218 can have a viscosity of at least 10,000 Poise. In yet other embodiments, the medicament 218 can have a viscosity of at least 100,000 Poise.

In some embodiments, the medicament 218 can be a fluid that is characterized by a substantially linear shear stress as a function of the rate of shear strain applied thereto. Said another way, in some embodiments, the medicament 218 can be a Newtonian fluid having a viscosity that varies substantially only as a function of its temperature and pressure. In other embodiments, the medicament 218 can be a fluid that is characterized by a non-linear shear stress as a function of the rate of shear strain applied thereto. Said another way, in some embodiments, the medicament 218 can be a non-Newtonian fluid having a viscosity that varies according other factors, such as, for example, the magnitude of and/or rate of increase of a force applied to the medicament 218.

The needle 220 is coupled to the medicament container 210 such that the needle 220 is in fluid communication with the first portion 215 of the medicament container 210. The needle 220 can be coupled to the medicament container 210 by any suitable mechanism. For example, in some embodiments, the needle 220 can be coupled to the medicament container 210 by a Luer fitting that provides a substantially fluid-tight seal (i.e., a seal that that substantially prevents a liquid and/or a gas from passing therethrough) between the needle 220 and the medicament container 210. In some embodiments, the fluid-tight seal can be a hermetic seal (i.e., a seal that substantially prevents a gas from passing therethrough).

The needle 220 can have any suitable bore size and length. For example, in some embodiments, the needle can have a small bore to reduce patient discomfort during a procedure. For example, in some embodiments, the needle 220 can define a lumen having a nominal inner diameter of less than or equal to approximately 0.191 millimeters (i.e., a 27 gauge needle). In other embodiments, the needle 220 can define a lumen having a nominal inner diameter of less than or equal to approximately 0.140 millimeters (i.e., a 30 gauge needle). In some embodiments, for example, the needle 220 can define a lumen having a nominal inner diameter of approximately 0.114 millimeters (i.e., a 31 gauge needle). In some embodiments, for example, the needle 220 can define a lumen having a nominal inner diameter of approximately 0.089 millimeters (i.e., a 32 gauge needle). In some embodiments, the needle 220 can have a length of at least 17 millimeters.

When the piston 214 moves within the medicament container 210, as shown by the arrow DD in FIG. 4, the medicament 218 is conveyed from the first portion 215 of the medicament container 210. Said another way, a user can inject the medicament 218 into a body by actuating the medical device 200 to cause the piston 214 to move distally within the medicament container 210. The energy source 250 is operatively coupled to the piston 214 such that the piston 214 can be moved non-manually. The energy source 250 can be any suitable form of energy configured produce kinetic energy to move the piston 214 within the medicament container 210. The amount of kinetic energy required to move the piston 214 within the medicament container 210 is dependent on, among other things, the viscosity of the medicament 218, the desired flow rate of the medicament 218 through the distal end portion 222 of the needle 220, the length of the needle 220 and/or the size of the lumen defined by the needle 220. In some embodiments, the energy source 250 can produce kinetic energy sufficient to move the piston 214 such that a medicament 218 having a viscosity of at least 1000 Poise can be injected through the distal end portion 222 of the needle at a flow rate of at least 0.02 cubic centimeters per minute. In other embodiments, the energy source 250 can produce kinetic energy sufficient to move the piston 214 such that a medicament 218 having a viscosity of at least 1000 Poise can be injected through the distal end portion 222 of the needle at a flow rate of at least 0.5 cubic centimeters per minute. In yet other embodiments, the energy source 250 can produce kinetic energy sufficient to move the piston 214 such that a medicament 218 having a viscosity of at least 10,000 Poise can be injected through the distal end portion 222 of the needle 220 at a flow rate of at least 0.5 cubic centimeters per minute. In still other embodiments, the energy source 250 can produce kinetic energy sufficient to move the piston 214 such that a medicament 218 having a viscosity of at least 10,000 Poise can be injected through the distal end portion 222 of the needle 220 at a flow rate of at least 3 cubic centimeters per minute. In still other embodiments, the energy source 250 can produce kinetic energy sufficient to move the piston 214 such that a medicament 218 having a viscosity of at least 10,000 Poise can be injected through the distal end portion 222 of the needle 220 at a flow rate of between 3 and 5 cubic centimeters per minute.

Additionally, the pressure of the medicament 218 within the medicament container 210 during an injection event is related to the kinetic energy applied to the piston 214, and is therefore also dependent on, among other things, the viscosity of the medicament 218, the desired flow rate of the medicament 218 through the distal end portion 222 of the needle 220, the length of the needle 220 and/or the size of the lumen defined by the needle 220. In certain circumstances, the pressure of the medicament 218 within the medicament container 210 can be modeled by the Hagen-Poiseuille law, as indicated below:

$$P = (8 * \mu * L * Q) / (\Pi * R4) \qquad (1)$$

where P is the pressure of the medicament 218 within the medicament container, $\mu$ is the viscosity of the medicament 218, L is the length of the needle 220, Q is the flow rate of the medicament 218 through the distal end portion 222 of the needle 220, and R is the radius of the lumen defined by the needle 220. Because the pressure required to inject a high viscosity fluid through a small-bore needle is proportional to the inverse of the radius of the lumen of the needle to the fourth power, the pressure of the medicament 218 within the medicament container 210 necessary to achieve the desired flow rate can, at times, be relatively high. In some embodiments, the energy source 250 can be configured to move the piston 214 within the medicament container 210 such that a pressure of the medicament 218 within the medicament container 210 is greater than 345 kilopascals (50 p.s.i.). In other embodiments, the energy source 250 can be configured to move the piston 214 within the medicament container 210 such that a pressure of the medicament 218 within the medicament container 210 is greater than 690 kilopascals (100 p.s.i.). In still other embodiments, the energy source 250 can be configured to move the piston 214 within the medicament container 210 such that a pressure of the medicament 218 within the medicament container 210 is greater than 1035 kilopascals (150 p.s.i.). In still other embodiments, the energy source 250 can be configured to move the piston 214 within the medicament container 210 such that a pressure of the medicament 218 within the medicament container 210 is greater than 34.5 Megapascals (5000 p.s.i.).

The regulator 260 is configured to regulate the flow rate of the medicament 218 through the distal end portion 222 of the needle 220. In this manner, the user can adjust the flow rate of the medicament 218 through the distal end portion 222 of the needle 220. In some embodiments, for example, the regulator 260 can substantially stop the flow of the medicament 218 through the distal end portion 222 of the needle 220. In this manner, as described above, the user can discontinuously inject the medicament 218 within the body.

The regulator 260 can be any suitable mechanism for regulating the flow rate of the medicament 218 through the distal end portion 222 of the needle 220. As described above, in some embodiments, the regulator 260 can control the transmission of energy from the energy source 250 to the piston 214. In other embodiments, the regulator 260 can selectively restrict the flow path of the medicament 218 within the first portion 215 of the medicament container 210 and/or the needle 220. The above system can provide soft tissue augmentation including breast implant, butt implant, facial rejuvenation, penile enhancement, and body reconstruction. The system allows for breast or butt enlargements to be made with fine attenuation. The system provides a naturally smooth skin without requiring complex surgery. The desired effect can be achieved quickly and with minimally invasive surgery. The risk of infection can be reduced due to the minimally invasive therapy. The gel material that filled the balloon is compliant at different frequencies with the surrounding tissue so that it matches the response of the tissue to the exterior touches, thus creating the natural feelings to touches at the site. The compliant nature of the gel filler makes the expression of the patient to appear more natural than other procedures by not distorting the natural the breast or butt contours. The filler material, being a higher molecular gel, allows an implant material such as halyuronic acid to be used which allows continuous zero order drug delivery method, the most desirable controlled delivery method.

The methods of the invention involve administering injections into the deep part of the skin (i.e., deep fat or just above the bone) using large injections of a hyaluronic acid composition that has been formulated for injection into the superficial part of the skin covering the breast or butt or buttock. One of skill in the art will appreciate that the depth at with the injection is made will vary depending on the specific injection site. Further, the injections can be administered without requiring large bore needles or surgical incisions, as the methods of the present invention utilize small bore needles. Preferably, the hyaluronic acid bolus is injected into the skin using a needle having a gauge of from 24 (0.559 mm) to 30 (0.305 mm), where the bolus is more preferably injected using a needle having a gauge of from 26 (0.457 mm) to 28 (0.356 mm), and is most preferably injected using a 27 gauge needle (0.406 mm). In other embodiments of this invention, the hyaluronic acid bolus can be injected using a small canullae from 1-2 mm in diameter to deliver larger bolus with higher viscosity.

In some embodiments of this invention, about 1.5 to 6, preferably about 3 to 4, full syringes (for example 0.7 cc or 0.8 cc syringes) can be injected on each side of the subject's facial rhytids to eleviate the wrinkles. It is preferred that at least 1 cc, more preferably at least 2 cc, even more preferably about 2 to 3 cc, are injected on each side. One of skill in the art will appreciate that the amount of hyaluronic acid to be injected will also vary depending on the specific injection site.

In other embodiments of this invention, about 50 to 400 cc, can be injected on each side of the subject's breast or buttocks to enhance its curvature. Again, one of skill in the art will appreciate that the amount of hyaluronic acid to be injected will also vary depending on the specific injection site.

In some embodiments, for example, an apparatus includes a 3D imaging system coupled to a computer that controls medical injector, a medicament container, a needle, an energy source, and a regulator. The medicament container has a piston movably disposed therein such that the medicament container is divided into a first portion and a second portion. The first portion of the medicament container is configured to contain a medicament, such as, for example a dermal filler. The needle is coupled to the medicament container such that the needle is in fluid communication with the first portion of the medicament container. The energy source is operatively coupled to the piston and is configured to produce a kinetic energy to move the piston within the medicament container such that the medicament having a viscosity of at least 1000 Poise (100 N-sec/m2) can be conveyed from the first portion of the medicament container through a distal end of the needle at a flow rate of at least 0.02 cubic centimeters per minute. The regulator is configured to regulate the flow rate of the medicament through the distal end of the needle.

In some embodiments, for example, an apparatus includes a 3D imaging system coupled to a computer that controls medical injector, a pressurized fluid source, and a regulator. The medical injector is configured to contain halyuronic acid filler, and includes a needle. The needle defines a lumen therethrough having a nominal inner diameter of less than approximately 0.140 millimeters (i.e., the needle is smaller than 30 gauge), and has a length of at least 17 millimeters. The pressurized fluid source, which can include, for example, a canister of pressurized fluid, is operatively coupled to the medical injector. A pressurized fluid from the pressurized fluid source has a pressure of at least 345 kilopascals. The pressurized fluid is configured to actuate the medical injector such that the dermal filler can be conveyed from the medical injector through the lumen of the needle. The regulator is configured to regulate the flow rate of the dermal filler through the lumen of the needle.

The term "hyaluronic acid" is used in literature to mean acidic polysaccharides with different molecular weights constituted by residues of D-glucuronic and N-acetyl-D-glucosamine acids, which occur naturally in cell surfaces, in the basic extracellular substances of the connective tissue of vertebrates, in the synovial fluid of the joints, in the endobulbar fluid of the eye, in human umbilical cord tissue and in cocks' combs.

The term "hyaluronic acid" is in fact usually used as meaning a whole series of polysaccharides with alternating residues of D-glucuronic and N-acetyl-D-glucosamine acids with varying molecular weights or even the degraded fractions of the same, and it would therefore seem more correct to use the plural term of "hyaluronic acids". The singular term will, however, be used all the same in this description; in addition, the abbreviation "HA" will frequently be used in place of this collective term.

"Hyaluronic acid" is defined herein as an unsulphated glycosaminoglycan composed of repeating disaccharide units of N-acetylglucosamine (GlcNAc) and glucuronic acid (GlcUA) linked together by alternating beta-1,4 and beta-1,3 glycosidic bonds. Hyaluronic acid is also known as hyaluronan, hyaluronate, or HA. The terms hyaluronan and hyaluronic acid are used interchangeably herein.

Rooster combs are a significant commercial source for hyaluronan. Microorganisms are an alternative source. U.S. Pat. No. 4,801,539 discloses a fermentation method for preparing hyaluronic acid involving a strain of *Streptococcus zooepidemicus* with reported yields of about 3.6 g of hyaluronic acid per liter. European Patent No. EP0694616 discloses fermentation processes using an improved strain of *Streptococcus zooepidemicus* with reported yields of about 3.5 g of hyaluronic acid per liter. As disclosed in WO 03/054163 (Novozymes), which is incorporated herein in its entirety, hyaluronic acid or salts thereof may be recombinantly produced, e.g., in a Gram-positive *Bacillus* host.

Hyaluronan synthases have been described from vertebrates, bacterial pathogens, and algal viruses (DeAngelis, P. L., 1999, Cell. Mol. Life Sci. 56: 670-682). WO 99/23227 discloses a Group I hyaluronate synthase from *Streptococcus equisimilis*. WO 99/51265 and WO 00/27437 describe a Group II hyaluronate synthase from *Pasteurella multocida*. Ferretti et al. discloses the hyaluronan synthase operon of *Streptococcus pyogenes*, which is composed of three genes, hasA, hasB, and hasC, that encode hyaluronate synthase, UDP glucose dehydrogenase, and UDP-glucose pyrophosphorylase, respectively (Proc. Natl. Acad. Sci. USA. 98, 4658-4663, 2001). WO 99/51265 describes a nucleic acid segment having a coding region for a *Streptococcus equisimilis* hyaluronan synthase.

Since the hyaluronan of a recombinant *Bacillus* cell is expressed directly to the culture medium, a simple process may be used to isolate the hyaluronan from the culture medium. First, the *Bacillus* cells and cellular debris are physically removed from the culture medium. The culture medium may be diluted first, if desired, to reduce the viscosity of the medium. Many methods are known to those skilled in the art for removing cells from culture medium, such as centrifugation or microfiltration. If desired, the remaining supernatant may then be filtered, such as by ultrafiltration, to concentrate and remove small molecule contaminants from the hyaluronan. Following removal of the cells and cellular debris, a simple precipitation of the hyaluronan from the medium is performed by known mechanisms. Salt, alcohol, or combinations of salt and alcohol may be used to precipitate the hyaluronan from the filtrate. Once reduced to a precipitate, the hyaluronan can be easily isolated from the solution by physical means. The hyaluronan may be dried or concentrated from the filtrate solution by using evaporative techniques known to the art, such as lyophilization or spraydrying.

The term "microbead" is used herein interchangeably with microdrop, microdroplet, microparticle, microsphere, nanobead, nanodrop, nanodroplet, nanoparticle, nanosphere etc. A typical microbead is approximately spherical and has an number average cross-section or diameter in the range of between 1 nanometer to 1 millimeter. Though, usually the microbeads of the one embodiment will be made with a desired size in a much more narrow range, i.e., they will be fairly uniform. The microbeads preferably have a diameter in the range of about 100-1,000 nanometer; or in the range of 1,000 nanometer to 1,000 micrometer. The size-distribution of the microbeads will be low and the polydispersibility narrow.

Host Cells

A preferred embodiment relates to the method of the first aspect, wherein the hyaluronic acid or salt thereof is recombinantly produced, preferably by a Gram-positive bacterium or host cell, more preferably by a bacterium of the genus *Bacillus*.

The host cell may be any *Bacillus* cell suitable for recombinant production of hyaluronic acid. The *Bacillus* host cell may be a wild-type *Bacillus* cell or a mutant thereof *Bacillus* cells useful in the practice of the one embodiment include, but are not limited to, *Bacillus agaraderhens, Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells. Mutant *Bacillus subtilis* cells particularly adapted for recombinant expression are described in WO 98/22598. Non-encapsulating *Bacillus* cells are particularly useful in the one embodiment.

In one embodiment, the *Bacillus* host cell is a *Bacillus amyloliquefaciens, Bacillus clausii, Bacillus lentus, Bacillus licheniformis, Bacillus stearothermophilus* or *Bacillus subtilis* cell. In a more preferred embodiment, the *Bacillus* cell is a *Bacillus amyloliquefaciens* cell. In another more preferred embodiment, the *Bacillus* cell is a *Bacillus clausii* cell. In another more preferred embodiment, the *Bacillus* cell is a *Bacillus lentus* cell. In another more preferred embodiment, the *Bacillus* cell is a *Bacillus licheniformis* cell. In another more preferred embodiment, the *Bacillus* cell is a *Bacillus subtilis* cell. In a most preferred embodiment, the *Bacillus* host cell is *Bacillus subtilis* A164Δ5 (see U.S. Pat. No. 5,891,701) or *Bacillus subtilis* 168Δ4.

Molecular Weight

The content of hyaluronic acid may be determined according to the modified carbazole method (Bitter and Muir, 1962, Anal Biochem. 4: 330-334). Moreover, the number average molecular weight of the hyaluronic acid may be determined using standard methods in the art, such as those described by Ueno et al., 1988, Chem. Pharm. Bull. 36, 4971-4975; Wyatt, 1993, Anal. Chim. Acta 272: 1-40; and Wyatt Technologies, 1999, "Light Scattering University DAWN Course Manual" and "DAWN EOS Manual" Wyatt Technology Corporation, Santa Barbara, Calif.

In one embodiment, the hyaluronic acid, or salt thereof, of the one embodiment has a molecular weight of about 10,000 to about 10,000,000 Da. In a more preferred embodiment it has a molecular weight of about 25,000 to about 5,000,000 Da. In a most preferred embodiment, the hyaluronic acid has a molecular weight of about 50,000 to about 3,000,000 Da.

In another embodiment, the hyaluronic acid or salt thereof has a molecular weight in the range of between 300,000 and 3,000,000; preferably in the range of between 400,000 and 2,500,000; more preferably in the range of between 500,000 and 2,000,000; and most preferably in the range of between 600,000 and 1,800,000.

In yet another embodiment, the hyaluronic acid or salt thereof has a low number average molecular weight in the range of between 10,000 and 800,000 Da; preferably in the range of between 20,000 and 600,000 Da; more preferably in the range of between 30,000 and 500,000 Da; even more preferably in the range of between 40,000 and 400,000 Da; and most preferably in the range of between 50,000 and 300,000 Da.

Salts and Crosslinked HA

One embodiment relates to a method of the first aspect, which comprises an inorganic salt of hyaluronic acid, preferably sodium hyaluronate, potassium hyaluronate, ammonium hyaluronate, calcium hyaluronate, magnesium hyaluronate, zinc hyaluronate, or cobalt hyaluronate.

Other Ingredients

In another embodiment, the product produced by the method of one embodiment may also comprise other ingredients, preferably one or more active ingredient, preferably one or more pharmacologically active substance, and also preferably a water-soluble excipient, such as lactose or a non-biologically derived sugar.

Non-limiting examples of an active ingredient or the one or more pharmacologically active substance(s) which may be used in the one embodiment include vitamin(s), anti-inflammatory drugs, antibiotics, bacteriostatics, general anaesthetic drugs, such as, lidocaine, morphine etc. as well as protein and/or peptide drugs, such as, human growth hormone, bovine growth hormone, porcine growth hormone, growth hormone releasing hormone/peptide, granulocyte-colony stimulating factor, granulocyte macrophage-colony stimulating factor, macrophage-colony stimulating factor, erythropoietin, bone morphogenic protein, interferon or derivative thereof, insulin or derivative thereof, atriopeptin-Ill, monoclonal antibody, tumor necrosis factor, macrophage activating factor, interleukin, tumor degenerating factor, insulin-like growth factor, epidermal growth factor, tissue plasminogen activator, factor IIV, factor IIIV, and urokinase.

A water-soluble excipient may be included for the purpose of stabilizing the active ingredient(s), such excipient may include a protein, e.g., albumin or gelatin; an amino acid, such as glycine, alanine, glutamic acid, arginine, lysine and a salt thereof; carbohydrate such as glucose, lactose, xylose, galactose, fructose, maltose, saccharose, dextran, mannitol, sorbitol, trehalose and chondroitin sulphate; an inorganic salt such as phosphate; a surfactant such as TWEEN® (ICI), poly ethylene glycol, and a mixture thereof. The excipient or stabilizer may be used in an amount ranging from 0.001 to 99% by weight of the product.

Several aspects of one embodiment relate to various compositions and pharmaceuticals comprising, among other constituents, an effective amount of the crosslinked HA product, and an active ingredient, preferably the active ingredient is a pharmacologically active agent; a pharmaceutically acceptable carrier, excipient or diluent, preferably a water-soluble excipient, and most preferably lactose.

In addition, aspects of one embodiment relate to articles comprising a product as defined in the first aspect or a composition as defined in the aspects and embodiments above, e.g., a sanitary article, a medical or surgical article. In a final aspect one embodiment relates to a medicament capsule or microcapsule comprising a product as defined in the first aspect or a composition as defined in other aspects and embodiments of one embodiment.

One method of producing crosslinked hyaluronic acid microbeads include:

(a) mixing an aqueous alkaline solution comprising hyaluronic acid, or a salt thereof, with a solution comprising a crosslinking agent;

(b) forming microdroplets having a desired size from the mixed solution of step (a) in an organic or oil phase to form a water in organic or water in oil (W/O) emulsion;

(c) continuously stirring the W/O emulsion, whereby the reaction of hyaluronic acid with divinylsulfone takes place to provide crosslinked hyaluronic acid microbeads; and (d) purifying the crosslinked hyaluronic acid microbeads.

It has previously been described how to produce hyaluronic acid recombinantly in a *Bacillus* host cell, see WO 2003/054163, Novozymes NS, which is incorporated herein in its entirety. The hyaluronic acid, or salt thereof, can also be recombinantly produced in a *Bacillus* host cell. Various molecular weight fractions of hyaluronic acid have been described as advantageous for specific purposes.

One embodiment relates to a method of the first aspect, wherein the hyaluronic acid, or salt thereof, has an number average molecular weight of between 100 and 3,000 kDa, preferably between 500 and 2,000 kDa, and most preferably between 700 and 1,800 kDa. The initial concentration of hyaluronic acid, or a salt thereof, in the method of one embodiment, influences the properties of the resulting crosslinked microbeads. Therefore, one embodiment relates to a method of the first aspect, wherein the alkaline solution comprises dissolved hyaluronic acid, or salt thereof, in a concentration of between 0.1%-40% (w/v).

The pH value during the crosslinking reaction also influences the outcome, so in a preferred embodiment one embodiment relates to a method of the first aspect, wherein the alkaline solution comprises dissolved sodium hydroxide in a concentration of between 0.001-2.0 M. The concentration of the crosslinking agent has a profound impact on the resulting microbeads.

Consequently, one embodiment relates to a method of the first aspect, wherein the crosslinking agent is divinylsulfone (DVS); preferably DVS is comprised in the mixed solution of step (a) in a weight ratio of between 1:1 and 100:1 of HA/DVS (dry weight), preferably between 2:1 and 50:1 of HA/DVS (dry weight).

Other crosslinking agents are also envisioned as being suitable for the methods of the one embodiment, such as, crosslinking agents based on bisepoxide crosslinking technology: GDE=glycerol diglycidyl ether and BDE: 1,4-butanediol diglycidyl ether.

Crosslinking agents suitable for the methods of the one embodiment are for example poly functional (>=2) OH-reactive compounds. Examples for suitable crosslinking agents are divinylsulfone (DVS) or crosslinking agents based on bisepoxide crosslinking technology, for example GDE=glycerol diglycidyl ether or BDE: 1,4-butanediol diglycidyl ether. The crosslinking agent is preferably selected from divinylsulfone, glycerol diglycidyl ether or 1,4-butanediol diglycidyl ether. The most preferred crosslinking agent of one embodiment is divinylsulfone which is preferably used in the weight ratio mentioned above.

An initial period of stirring during and/or immediately after mixing the solution comprising the crosslinking agent and the HA-solution was desirable to achieve satisfactory gelling. Accordingly, one embodiment relates to a method of the first aspect, wherein the reaction of hyaluronic acid with divinylsulfone takes place at a temperature in the range of 5° C.-100° C., preferably in the range of 15° C.-50° C., more preferably in the range of 20° C.-30° C. In another preferred embodiment, the stirring in step (c) is continued for a period of between 1-180 minutes.

A heating step can be beneficial after mixing the solutions. Accordingly, the mixed solution is heated to a temperature in the range of 20° C.-100° C., preferably in the range of 25° C.-80° C., more preferably in the range of 30° C.-60° C., and most preferably in the range of 35° C.-55° C., and the temperature is maintained in this range for a period of at least 5 minutes, preferably at least 10 minutes, 20 minutes, 30, 40, 50, 60, 70, 80, 90, 100, 110, 120, 130, 140, 150, 160, 170, or most preferably at least 180 minutes after mixing the solutions; preferably without stirring.

It is advantageous to leave the reaction mixture at room temperature for a brief period after the crosslinking reaction has taken place, but still with continuous stirring.

In one embodiment, the reaction mixture is maintained after the reaction has taken place for a period of at least 5 minutes, preferably at least 10 minutes, 20 minutes, 30, 40, 50, 60, 70, 80, 90, 100, 110, 120, 130, 140, 150, 160, 170, or most preferably at least 180 minutes, at a temperature in the range of 0° C.-40° C., preferably in the range of 10° C.-30° C. It might by advantageous when the microdroplets of step (b) have a number average diameter in the range of from about 1 nanometer to 1 millimeter. The maximum of the particle size distribution of the microdroplets of step (b) is preferably in the range of from 0.1 to 100 pm, more preferably from 0.5 to 10 μm and most preferably from 1 to 2 μm. The size of the droplets can be adjusted by the choice of emulsifier used and the intensity of stirring. The combination of emulsifier used and intensity of stirring necessary to obtain droplets with the desired size can be determined by simple test series. The microdroplets can have a number average diameter in the range of about 1 nanometer to 1 millimeter. It is also preferred that the crosslinked microbead of the second aspect has a number average diameter in the range of about 1 nanometer to 1 millimeter. It might be advantageous to obtain a dispersion in step (c) that comprises almost none unreacted crosslinking agent. Preferably the dispersion more preferably the microbeads comprise less than 10 ppm by weight (wppm), more preferably less than 5 wppm. The concentration of free crosslinking agent in the dispersion especially needs to be low if the dispersion is directly used in pharmaceutical or biomedical application/device compositions because the unreacted crosslinking agent might be a toxicological threat. It is therefore preferred to last the reaction of step (c) till a dispersion is obtained comprising the unreacted crosslinking agent in the concentration mentioned above.

Compounds from at least one of the following groups can be employed as nonionic emulsifiers or surfactants: addition products of from 2 to 100 mol of ethylene oxide and/or 0 to 5 mol of propylene oxide on linear fatty alcohols having 8 to 22 C atoms, on fatty acids having 12 to 22 C atoms and on alkylphenols having 8 to 15 C atoms in the alkyl group, C12/18-fatty acid mono- and diesters of addition products of from 1 to 100 mol of ethylene oxide on glycerol, glycerol mono- and diesters and sorbitan mono- and diesters of saturated and unsaturated fatty acids having 6 to 22 carbon atoms and ethylene oxide addition products thereof, alkyl mono- and oligoglycosides having 8 to 22 carbon atoms in the alkyl radical and ethylene oxide addition products thereof, addition products of from 2 to 200 mol of ethylene oxide on castor oil and/or hydrogenated castor oil, partial esters based on linear, branched, unsaturated or saturated C6-C22-fatty acids, ricinoleic acid and 12-hydroxystearic acid and glycerol, polyglycerol, pentaerythritol, dipentaerythritol, sugar alcohols (e.g. sorbitol), alkyl glucosides (e.g. methyl glucoside, butyl glucoside, lauryl glucoside) and polyglucosides (e.g. cellulose), mono-, di- and trialkyl phosphates and mono-, di- and/or tri-PEG-alkyl phosphates and salts thereof, polysiloxane/polyether copolymers (Dimethicone Copolyols), such as e.g. PEG/PPG-20/6 Dimethicone, PEG/PPG-20/20 Dimethicone, Bis-PEG/PPG-20/20 Dimethicone, PEG-12 or PEG-14 Dimethicone, PEG/PPG-14/4 or 4/12 or 20/20 or 18/18 or 17/18 or 15/15, polysiloxane/polyalkyl polyether copolymers and corresponding derivatives, such as e.g. Lauryl or Cetyl Dimethicone Copolyols, in particular Cetyl PEG/PPG-10/1 Dimethicone (ABIL® EM 90 (Evonik Degussa)), mixed esters of pentaerythritol, fatty acids, citric acid and fatty alcohol according to DE 11 65 574 and/or mixed esters of fatty acids having 6 to 22 carbon atoms, methylglucose and polyols, such as e.g. glycerol or polyglycerol, citric acid esters, such as e.g. Glyceryl Stearate Citrate, Glyceryl Oleate Citrate and Dilauryl Citrate.

Preferred emulsifiers used in the one embodiment are selected from those having a HLB-value of from 3 to 9, preferably 4 to 6 and more preferably about 5. Preferred emulsifiers are selected from polyglyceryl-4-diisostearat/polyhydroxysterat/sebacat (ISOLAN® GPS), PEG/PPG-10/1 dimethicone, (ABIL® EM 90), Polyglyceryl-4 Isostearate (ISOLAN® GI 34), Polyglyceryl-3 Oleate (ISOLAN® GO 33), Methylglucose Isostearate (ISOLAN® IS), Diisostearoyl Polyglyceryl-3 Dimer Dilinoleate (ISOLAN® PDI), Glyceryl Oleate (TEGIN® O V), Sorbitan Laurate (TEGO® SML), Sorbitan Oleate (TEGO® SMO V) and Sorbitan Stearate (TEGO® SMS). These preferred emulsifiers are available from Evonik Goldschmidt GmbH.

Anionic emulsifiers or surfactants can contain groups which confer solubility in water, such as e.g. a carboxylate, sulphate, sulphonate or phosphate group and a lipophilic radical. Anionic surfactants which are tolerated by skin are known in large numbers to the person skilled in the art and are commercially obtainable. In this context these can be alkyl sulphates or alkyl phosphates in the form of their alkali metal, ammonium or alkanolammonium salts, alkyl ether-sulphates, alkyl ether-carboxylates, acyl sarcosinates and sulphosuccinates and acyl glutamates in the form of their alkali metal or ammonium salts.

Cationic emulsifiers and surfactants can also be added. Quaternary ammonium compounds, in particular those provided with at least one linear and/or branched, saturated or unsaturated alkyl chain having 8 to 22 C atoms, can be employed in particular as such, thus, for example, alkyltrimethylammonium halides, such as e.g. cetyltrimethylammonium chloride or bromide or behenyltrimethylammonium chloride, but also dialkyldimethylammonium halides, such as e.g. distearyldimethylammonium chloride.

Monoalkylamidoquats, such as e.g. palmitamidopropyltrimethylammonium chloride, or corresponding dialkylamidoquats can furthermore be employed. Readily biodegradable quaternary ester compounds, which can be quaternized fatty acid esters based on mono-, di- or triethanolamine, can furthermore be employed. Alkylguanidinium salts can furthermore be admixed as cationic emulsifiers.

Typical examples of mild surfactants, i.e. surfactants which are particularly tolerated by skin, are fatty alcohol polyglycol ether-sulphates, monoglyceride sulphates, mono- and/or dialkyl sulphosuccinates, fatty acid isethionates, fatty acid sarcosinates, fatty acid taurides, fatty acid glutamates, ether-carboxylic acids, alkyl oligoglucosides, fatty acid glucamides, alkylamidobetaines and/or protein-fatty acid condensates, the latter for example based on wheat proteins.

It is furthermore possible to employ amphoteric surfactants, such as e.g. betaines, amphoacetates or amphopropionates, thus e.g. substances such as the N-alkyl-N, N-dimethylammonium glycinates, for example coco-alkyldimethylammonium glycinate, N-acylaminopropyl-N, N-dimethylammonium glycinates, for example coco-acylamimopropyldimethylammonium glycinate, and 2-alkyl-3-carboxymethyl-3-hydroxyethylimidazolines having in each case 8 to 18 C atoms in the alkyl or acyl group, and coco-acylaminoethylhydroxyethylcarboxymethyl glycinate.

Of the ampholytic surfactants, those surface-active compounds which contain, apart from a C8/18-alkyl or -acyl group, at least one free amino group and at least one —COOH or —SO3H group in the molecule and are capable of formation of inner salts can be employed. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 C atoms in the alkyl group. Further examples of ampholytic surfactants are N-coco-alkylaminopropionate, coco-acylaminoethylaminopropionate and 012/18-acrylsarcosine.

Preferred emulsifiers or surfactants used for formulating the composition are identical to those used in the production of the microbeads.

Many types of buffers or acids, as are well known to the skilled person, have been envisioned as suitable for the swelling and neutralizing of the crosslinked microbeads of one embodiment. In a preferred embodiment the buffer comprises a buffer with a pH value in the range of 2.0-8.0, preferably in the range of 5.0-7.5.

Optimally, a suitable buffer is chosen with a pH value, which results in that the crosslinked microbeads have a pH value as close to neutral as possible. In one embodiment, the buffer comprises a buffer with a pH value, which results in that the crosslinked microbeads have a pH value between 5.0 and 7.5. The buffer can be a phosphate buffer and/or a saline buffer. The crosslinked microbeads can be washed at least once with water, water and an acid, water and a phosphate buffer, water and a saline buffer, or water and a phosphate buffer and a saline buffer, with a pH value in the range of 2.0-8.0, preferably in the range of 5.0-7.5. The purifying step may comprise any separation technique known in the art, e.g. filtration, decantation, centrifugation and so on. It might be advantageous to combine one or more purifying steps with one or more neutralizing steps.

The purifying step can include dialyzing the crosslinked microbeads against de-ionized water using a dialysis membrane that allows free diffusion of molecules having a size less than 13,000 Daltons. Standard emollients used in cosmetic or personal care formulations as oil phase can be added. Such standard emollients are not hydrocarbons or aromatic hydrocarbons, especially not toluene, o-xylene, dodecane, heptane, isooctane or cetylethylhexanoate. Preferred emollients used in the one embodiment are selected from mono- or diesters of linear and/or branched mono- and/or dicarboxylic acids having 2 to 44 C atoms with linear and/or branched saturated or unsaturated alcohols having 1 to 22 C atoms, the esterification products of aliphatic difunctional alcohols having 2 to 36 C atoms with monofunctional aliphatic carboxylic acids having 1 to 22 C atoms, long-chain aryl acid esters, such as e.g. esters of benzoic acid with linear and/or branched C6-C22-alcohols, or also benzoic acid isostearyl ester, benzoic acid butyloctyl ester or benzoic acid octyldodecyl ester, carbonates, preferably linear C6-C22-fatty alcohol carbonates, Guerbet carbonates, e.g. dicaprylyl carbonate, diethylhexyl carbonate, longer-chain triglycerides, i.e. triple esters of glycerol with three acid molecules, at least one of which is longer-chain, triglycerides based on C6-C10-fatty acids, linear or branched fatty alcohols, such as oleyl alcohol or octyldodecanol, and fatty alcohol ethers, such as dialykl ether e. g. dicaprylyl ether, silicone oils and waxes, e.g. polydimethylsiloxanes, cyclomethylsiloxanes, and aryl- or alkyl- or alkoxy-substituted polymethylsiloxanes or cyclomethylsiloxanes, Guerbet alcohols based on fatty alcohols having 6 to 18, preferably 8 to 10 carbon atoms, esters of linear C6-C22 fatty acids with linear C6-C22-fatty alcohols, esters of branched C6-C13-carboxylic acids with linear C6-C22-fatty alcohols, esters of linear C6-C22-fatty acids with branched C8-C18-alcohols, in particular 2-ethylhexanol or isononanol, esters of branched C6-C13-carboxylic acids with branched alcohols, in particular 2-ethylhexanol or isononanol, esters of linear and/or branched fatty acids with polyhydric alcohols (such as e.g. propylene glycol, dimer diol or trimer triol) and/or Guerbet alcohols, liquid mono-/di-/triglyceride mixtures based on C6-C18-fatty acids, esters of C6-C22-fatty alcohols and/or Guerbet alcohols with aromatic carboxylic acids, plant oils, branched primary alcohols, substituted cyclohexanes, ring-opening products of epoxidized fatty acid esters with polyols and/or silicone oils or a mixture of two or more of these compounds. The emollient used is preferably not miscible with water without phase separation.

Monoesters which are suitable as emollients and oil components are e.g. the methyl esters and isopropyl esters of fatty acids having 12 to 22 C atoms, such as e.g. methyl laurate, methyl stearate, methyl oleate, methyl erucate, isopropyl myristate, isopropyl palmitate, isopropyl stearate, isopropyl oleate. Other suitable monoesters are e.g. n-butyl stearate, n-hexyl laurate, n-decyl oleate, isooctyl stearate, isononyl palmitate, isononyl isononanoate, 2-ethylhexyl laurate, 2-ethylhexyl palmitate, 2-ethylhexyl stearate, 2-hexyldecyl stearate, 2-octyldodecyl palmitate, oleyl oleate, oleyl erucate, erucyl oleate and esters which are obtainable from technical-grade aliphatic alcohol cuts and technical-grade aliphatic carboxylic acid mixtures, e.g. esters of unsaturated fatty alcohols having 12 to 22 C atoms and saturated and unsaturated fatty acids having 12 to 22 C atoms, such as are accessible from animal and plant fats. However, naturally occurring monoester and wax ester mixtures such as are present e.g. in jojoba oil or in sperm oil are also suitable. Suitable dicarboxylic acid esters are e.g. di-n-butyl adipate, di-n-butyl sebacate, di-(2-ethylhexyl) adipate, di-(2-hexyldecyl) succinate, di-isotridecyl azelate. Suitable diol esters are e.g. ethylene glycol dioleate, ethylene glycol di-isotridecanoate, propylene glycol di-(2-ethylhexanoate), butanediol di-isostearate, butanediol di-caprylate/caprate and neopentyl glycol di-caprylate. Fatty acid triglycerides can be used; as such, for example, natural plant oils, e.g. olive oil, sunflower oil, soya oil, groundnut oil, rapeseed oil, almond oil, sesame oil, avocado oil, castor oil, cacao butter, palm oil, but also the liquid contents of coconut oil or of palm kernel oil, as well as animal oils, such as e.g. shark-fish liver oil, cod liver oil, whale oil, beef tallow and butter-fat, waxes, such as beeswax, carnauba palm wax, spermaceti, lanolin and neat's foot oil, the liquid contents of beef tallow or also synthetic triglycerides of caprylic/capric acid mixtures, triglycerides from technical-grade oleic acid, triglycerides with isostearic acid, or from palmitic acid/oleic acid mixtures, can be employed as emollients (oil phase). Ghe organic or oil-phase can be mineral oil or TEGOSOFT® M. Preferably, the emulsifier is chosen from polyoxyethylene sorbitan fatty acid esters, sucrose fatty acid esters, sorbitan fatty acid esters, polysorbates, polyvinyl alcohol, polyvinyl pyrrolidone, gelatin, lecithin, poly-oxyethylene castor oil derivatives, tocopherol, tocopheryl polyethylene glycol succinate, tocopherol palmitate and tocopherol acetate, polyoxyethylene-polyoxypropylene co-polymers, or their mixtures.

The microbeads of one embodiment give access to the compositions of one embodiment comprising these microbeads. The compositions of one embodiment may comprise at least one additional component chosen from the group of emollients, emulsifiers and surfactants, thickeners/viscosity regulators/stabilizers, UV light protection filters, antioxidants, hydrotropic agents (or polyols), solids and fillers, film-forming agents, insect repellents, preservatives, conditioning agents, perfumes, dyestuffs, biogenic active compounds, moisturizers and solvents. The additional components might be inside and/or outside the microbeads. Preferably the additional ingredients are present in the composition of one embodiment outside or within the microbeads.

The composition of one embodiment can be an emulsion, a suspension, a solution, a cream, an ointment, a paste, a gel, an oil, a powder, an aerosol, a stick or a spray. The microbeads or the compositions of one embodiment may be used as a transdermal drug delivery system/vehicle. When applied topically the microbeads congregate in wrinkles and folds of the skin.

In another aspect, a method of producing a hydrogel comprising hyaluronic acid, or salt thereof, crosslinked with divinylsulfone (DVS) by (a) providing an alkaline solution of hyaluronic acid, or salt thereof;

(b) adding DVS to the solution of step (a), whereby the hyaluronic acid, or salt thereof, is crosslinked with the DVS to form a gel;

(c) treating the gel of step (b) with a buffer, wherein the gel swells and forms a hydrogel comprising hyaluronic acid, or salt thereof, crosslinked with DVS.

The hyaluronic acid, or salt thereof, has an average molecular weight of between 100 and 3,000 kDa, preferably between 500 and 2,000 kDa, and most preferably between 700 and 1,800 kDa. The initial concentration of hyaluronic acid, or a salt thereof, influences the properties of the resulting crosslinked gel, and of the swollen hydrogel. The alkaline solution comprises dissolved hyaluronic acid, or salt thereof, in a concentration of between 0.1%-40% (w/v). The pH value during the crosslinking reaction also influences the outcome, so in a preferred embodiment the invention relates to a method of the first aspect, wherein the alkaline solution comprises dissolved sodium hydroxide in a concentration of between 0.001-2.0 M. The concentration of the crosslinking agent can have a profound impact on the resulting gels. DVS is added to the solution of step (a) in a weight ratio of between 1:1 and 100:1 of HA/DVS (dry weight), preferably between 2:1 and 50:1 of HA/DVS (dry weight). An initial period of stirring during and/or immediately after adding the DVS to the HA-solution can be desirable to achieve satisfactory gelling. DVS is added with stirring to the solution of step (a), and wherein the solution temperature is maintained in the range of 5° C.-50° C., preferably in the range of 15° C.-40° C., more preferably in the range of 20° C.-30° C.; preferably the stirring is continued for a period of between 1-180 minutes. The DVS can be added without stirring to the solution of step (a).

The solution can be heated to a temperature in the range of 20° C.-100° C., preferably in the range of 25° C.-80° C., more preferably in the range of 30° C.-60° C., and most preferably in the range of 35° C.-55° C., and wherein the temperature is maintained in this range for a period of at least 5 minutes, preferably at least 10 minutes, 20 minutes, 30, 40, 50, 60, 70, 80, 90, 100, 110, 120, 130, 140, 150, 160, 170, or most preferably at least 180 minutes; preferably without stirring.

It is advantageous to leave the gel standing at room temperature for a brief period after the crosslinking reaction has taken place. The gel is maintained for a period of at least 5 minutes, preferably at least 10 minutes, 20 minutes, 30, 40, 50, 60, 70, 80, 90, 100, 110, 120, 130, 140, 150, 160, 170, or most preferably at least 180 minutes, at a temperature in the range of 0° C.-40° C., preferably in the range of 10° C.-30° C.

Many types of buffers, as are well known to the skilled person, have been envisioned as suitable for the swelling and neutralizing of the crosslinked gel of the invention. In a preferred embodiment the buffer comprises a buffer with a pH value in the range of 2.0-8.0, preferably in the range of 5.0-7.5. Optimally, a suitable buffer is chosen with a pH value, which results in that the swollen hydrogel has a pH value as close to neutral as possible. In a preferred embodiment, the buffer comprises a buffer with a pH value, which results in that the hydrogel has a pH value between 5.0 and 7.5. The buffer can be a phosphate buffer and/or a saline buffer. In the swelling step the buffer must have a sufficient volume for it to accommodate the swelling gel until the gel is fully swollen. The buffer in step (c) has a volume of at least 3 times the volume of the gel of step (b).

The swelling in step (c) is carried out at a temperature of between 20° C.-50° C. for a period of at least 5 minutes, preferably at least 10 minutes, 20 minutes, 30, 40, 50, 60, 70, 80, 90, 100, 110, 120, 130, 140, 150, 160, 170, or most preferably at least 180 minutes.

The hydrogel formed in step (c) can be washed at least once with water, water and a phosphate buffer, water and a saline buffer, or water and a phosphate buffer and a saline buffer, with a pH value in the range of 2.0-8.0, preferably in the range of 5.0-7.5.

It should be understood that various alternatives to the embodiments of the present exemplary system and method described herein may be employed in practicing the present exemplary system and method. It is intended that the following claims define the scope of the invention and that the system and method within the scope of these claims and their equivalents be covered thereby.

The implant properties can be adjusted by varying the above factors, among others. It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

What is claimed is:

1. A method to perform cosmetic enhancements using a body sensor to provide body patient data to a processor and an injector controlled by the processor to inject filler into a patient, comprising
    capturing a 3D model of a patient body portion using one or more cameras;
    modeling shape and size change in the body portion due to an implant;
    iteratively changing modeled body shapes or sizes until the patient is satisfied with a desired shape or size;
    controlling the injector to deliver the implant in the patient; and
    monitoring injection into patient and providing feedback if needed to achieve the desired shape and size.

2. The method of claim 1, comprising morphing or project the shape/size of breast or butt increase onto the 3D model of patient.

3. The method of claim 1, comprising allowing a user to select from a library of wardrobes to provide realistic post-implant simulation.

4. The method of claim 1, comprising injecting a polymer into a shell of a soft tissue human implant prior to or during implantation of the shell with a lumen in a human body.

5. The method of claim 1, comprising cross-linking the polymer, wherein a cross linking reaction occurs outside a shell or in-situ inside the shell.

6. The method of claim 1, wherein the polymer comprises one of: collagens, hyaluronic acids, celluloses, proteins, saccharides.

7. The method of claim 1, wherein the polymer comprises an extracellular matrix of a biological system.

8. The method of claim 1, comprising using cross linkers and forming homo-polymers or to form copolymers by crosslinking with other polymer species.

9. The method of claim 1, comprising controlling drug releases at predetermined timing in anticipation of an onset of a negative physiological event in response to invading foreign bodies.

10. The method of claim 1, comprising injecting anesthetics, lidocaine or compound to reduce or eliminate acute inflammatory reactions to the pharmaceutical substance.

11. The method of claim 1, comprising adding one or more compositions selected from the group consisting of steroids, corticosteroids, dexamethasone, triamcinolone.

12. An apparatus, comprising:
a processor;
a body sensor to provide body patient data to the processor; and
an injector controlled by the processor to inject filler into a patient.

13. The apparatus of claim 12, wherein the injector includes a medicament container, a needle, an energy source, and a regulator.

14. The apparatus of claim 13, wherein the injector medicament container has a piston movably disposed therein such that the medicament container is divided into a first portion and a second portion.

15. The apparatus of claim 14, wherein the first portion of the medicament container is configured to contain a filler, wherein the needle is coupled to the medicament container such that the needle is in fluid communication with the first portion of the medicament container.

16. The apparatus of claim 1, comprising a mechanical pump to inject the biocompatible cross-linked polymer under soft tissue in a minimally invasive manner.

17. The apparatus of claim 12, wherein the processor optimizes degradation profile of the composition and minimizing migration of the composition.

18. The apparatus of claim 12, wherein the filler has a predetermined number average molecular weight (Mn) and the polydispersity index, wherein the filler maintains a consistency of the composition in particle size and population densities, and wherein the filler comprises co-cross-linked glycosaminoglycan chemically with at least one other polymer including hyaluronan or hylan.

19. The apparatus of claim 12, wherein the processor continuously updates the current shape of breast or butt from a 3D model of the patient to fit to a desired shape.

20. The apparatus of claim 12, wherein the body sensor comprises a contact sensor or a contactless sensor.

* * * * *